US011026455B2

United States Patent
Gasser

(10) Patent No.: US 11,026,455 B2
(45) Date of Patent: Jun. 8, 2021

(54) ARTICLE OF CLOTHING INCORPORATING AT LEAST ONE CONDUCTIVE WIRE AND ASSOCIATED PRODUCTION METHOD

(71) Applicant: Sarl SP, Voiron (FR)

(72) Inventor: Jerome Gasser, Villeurbanne (FR)

(73) Assignee: Sarl SP, Voiron (FR)

( * ) Notice: Subject to any disclaimer, the term of this patent is extended or adjusted under 35 U.S.C. 154(b) by 0 days.

(21) Appl. No.: 16/966,629

(22) PCT Filed: Feb. 20, 2019

(86) PCT No.: PCT/EP2019/054152
§ 371 (c)(1),
(2) Date: Jul. 31, 2020

(87) PCT Pub. No.: WO2019/162295
PCT Pub. Date: Aug. 29, 2019

(65) Prior Publication Data
US 2021/0015180 A1    Jan. 21, 2021

(30) Foreign Application Priority Data
Feb. 21, 2018    (FR) ...................... 1851471

(51) Int. Cl.
*A41D 1/00* (2018.01)
*A41D 13/005* (2006.01)
*H05B 3/34* (2006.01)

(52) U.S. Cl.
CPC ......... *A41D 1/005* (2013.01); *A41D 13/0051* (2013.01); *H05B 3/342* (2013.01)

(58) Field of Classification Search
CPC .... A41D 1/005; A41D 13/0051; A41D 27/10; A41D 27/145; A41D 27/24; A41D 27/245; A41D 27/08; A41D 19/01535; H05B 3/342; H05B 3/34; H05B 3/36; H05B 3/345; H05B 3/347; H05B 3/38; H05B 3/64; H05B 1/0238; H05B 1/0252; H05B 2203/002; H05B 2203/003; H05B 2203/004; H05B 2203/01; H05B 2203/011; H05B 2203/014; H05B 2203/015; H05B 2203/029; H05B 2203/036
See application file for complete search history.

(56) References Cited

FOREIGN PATENT DOCUMENTS

| EP | 0128103 | 12/1984 |
|---|---|---|
| EP | 3252195 | 12/2017 |
| JP | 2013189729 | 9/2013 |
| JP | 5326316 | 10/2013 |

*Primary Examiner* — Shawntina T Fuqua
(74) *Attorney, Agent, or Firm* — Forge IP, PLLC

(57) ABSTRACT

An article of clothing having at least one conductive wire suitable for transmitting an electric current and at least one flat seam is disclosed. The seam includes at least two substantially parallel edging wires; at least one connecting wire disposed in a flat and serpentine manner between said edging wires; the connecting wire having bends connected alternately to the edging wires; the connecting wire corresponding to the at least one metal wire; and at least one other connecting wire extending in a separate plane from the connecting wire disposed in a flat manner.

12 Claims, 4 Drawing Sheets

ARTICLE OF CLOTHING INCORPORATING AT LEAST ONE CONDUCTIVE WIRE AND ASSOCIATED PRODUCTION METHOD

TECHNICAL FIELD

The present invention relates to an article of clothing having at least one conductive wire suitable for transmitting an electric current and/or to heat said clothing by Joule effect.

The invention finds a particularly advantageous application in forming a new type of clothing having a heating network incorporated into the clothing or having an electrical circuit incorporated into the clothing.

The practical applications of this invention are numerous and cover a great number of domains such as winter sports clothing, clothing incorporating light signals, clothing for physiological analysis, etc.

PRIOR ART

Solutions to incorporate conductive wires in fabrics have been sought for a long time.

E.g., in the domain of physiological analysis, document EP 0128103 discloses the manufacture of a bathing suit incorporating physiological sensors. A network of conductive wires is fixed on the bathing suit to transmit the information from the physiological sensors to an analyzer box. The conductive wires are laid on the bathing suit and fixed on it by non-conductive wires.

This method of attaching the conductive wires is particularly delicate to achieve without damaging the conductive wires while guaranteeing an effective attachment of the conductive wires on the clothing.

Additionally, this method of attachment generally degrades the aesthetic aspect of the clothing because the conductive wire is an added feature that is not incorporated into the structure of the clothing.

In the domain of clothing adornment, metal wires are used to form decorative motifs on the surface of a fabric. In the same way, these decorative metal wires are fixed by a seam affixed on the metal wire.

It is also known to make antistatic clothing to remove electrostatic charges throughout a clothing. To this end, document JP 2009228161 proposes to replace weft wires and warp wires of a fabric with metal wires so as to form a conductive network of electrostatic currents in the clothing.

However, these metal wires are a very small part of the invention because they must be incorporated into the thickness of the fabric. Thus, these wires can conduct only a few electrical charges, e.g. electrostatic charges, and they are not suitable for transmitting an electrical current. Additionally, there is a high risk of creating microshorts in the metal wire when inserting the wire into the fabric or when using the clothing.

To overcome this problem document JP 2009228161 uses a large number of overlapping metal wires.

Thus, the weft and warp structure of the conductive network is not suitable for producing a localized and isolated electrical circuit but for producing a large contact surface that allows for electrostatic discharge.

Additionally, document EP 3 252 195 discloses a conductive wire laid on a set of two fabrics and whereupon a seam is formed in order to fix the conductive wire on the two fabrics. This document discloses more specifically the connection of this conductive wire with a component allowing physiological measurements to be carried out. This connection is embodied by heating or applying ultrasounds on the conductive wire in order to dissolve the sheath and to electronically connect the conductive wire with a conductive fabric connected to the physiological measurement components.

In an embodiment of this document, a conductive wire is arranged sinusoidally on a set of two fabrics and edging wires are disposed on both sides of the loops of the conductive wire in order to fix the conductive wire on the set of two fabrics. However, this embodiment is particularly complex to implement since the seam must be sewn after the positioning of the conductive wire and the conductive wire must be maintained while the seam is being sewn.

The technical problem of the invention is to obtain an article of clothing, more easily attainable, incorporating at least one conductive wire having a sufficient cross-section to carry up to several watts of electrical power while limiting the mechanical stresses of the conductive wire so as to reduce the risk of microshorts.

DISCLOSURE OF THE INVENTION

The present invention is the result of a discovery whereby the connecting wire of a flat seam is particularly suitable for disposing a conductive wire because this connecting wire is laid flat having a sinusoidal shape whose bends are large enough to limit mechanical stresses on the conductive wire.

A flat seam is also called a "Flat Lock" or "Over Lock" seam in Anglo-Saxon literature. It is generally used to join pieces of fabric edge-to-edge without creating extra thickness by allowing great flexibility of the fabrics relative to each other.

To this end, this flat seam incorporates a first edging wire sewn on a first fabric and a second edging wire sewn on a second fabric. A connecting wire is laid flat having a sinusoidal shape at the junction between the two fabrics. The edging wires pass over the local ends of the bonding wire so as to attach each side of the connecting wire to a discrete fabric. The flat seam also incorporates at least one other connecting wire extending in a discrete plane from said connecting wire laid flat. It is therefore a flat seam incorporating 4 wires, 5 wires, or more.

This type of flat seam is known from class 600 of the NF ISO 4915 standard of November 2015. E.g., the invention may be implemented for points 602, 603, 604, 605, 606, 607, 608 and 609 of the NF ISO 4915 standard of November 2015.

This type of flat seam is very flexible and is particularly suitable for connecting stretchy fabrics.

Thus, a flat seam which has a conductive wire rather than the connecting wire between two edging wires makes it possible to incorporate a conductive wire into an article of clothing without degrading the aesthetics of the clothing because the conductive wire is contained in the seam.

Additionally, the use of the conductive wire in the flat seam makes it possible to use a conductive wire having a cross-section sufficient to carry electrical charges bearing a large power range and can be fitted/insulated to protect the wearer of the clothing against possible short-circuiting.

The use of an insulated wire also makes it possible to cross several wires with no risk of short-circuiting. The risk of micro-shorts is also reduced because the conductive wire has a significant degree of freedom in case of deformation of the flat seam due to the shape of the flat seam.

According to a first aspect, the invention relates to an article of clothing comprising at least one conductive wire suitable for transmitting an electrical current.

The invention is characterized in that said article of clothing contains at least one flat seam incorporating:
- at least two edging wires, substantially parallel;
- at least one connecting wire laid flat and in a serpentine configuration between said edging wires; said connecting wire having bends alternatively connected to said edging wires; said connecting wire corresponding to said at least one metal wire; and
- at least one other connecting wire extending in a discrete plane of said connecting wire laid flat.

For the purposes of the invention, an article of clothing means a finished or semi-finished feature forming a clothing, or a clothing as a whole. This article of clothing can be made by any known materials: weft and warp, knit, non-woven, etc.

Thus, the flat seam of the invention may be arranged in the center of a piece of fabric forming a clothing, e.g. to achieve a decorative design in addition to transporting electrical energy. The flat seam of the invention may also enable the assembly of different panels forming the article of clothing.

The invention makes it possible to produce a conductive electrical network on a clothing in order to transmit an electrical signal and/or to heat the clothing by Joule effect. Additionally, the electrical wires can be insulated to protect the wearer of the clothing.

According to one embodiment, said at least one connecting wire laid flat and in a serpentine configuration between said edging wires is made by juxtaposition of at least two metal wires. This embodiment makes it possible to increase the electrical powers that can be transported by the flat seam because the set of several metal wires increases the general cross-section of the conductors present in the flat seam.

E.g., each wire may correspond to a copper wire or a copper alloy, such as CuNi2, CuNi6, CuNi10, CuZn30, CuNi44, CuN23Mn, CuSn6, Cu materials, etc. The cross-section diameter of the wire can be between 0.02 mm and 0.4 mm preferably close to 0.2 mm. The wire may be enameled to provide electrical insulation, e.g. enameled protection may be grade 1 to 3.

According to one embodiment, said at least one other connecting wire corresponds to a metal wire. This embodiment makes it possible to produce at least a part of a flat seam having a resistivity different from another part of a flat seam wherein the other connecting wire is less conductive. By modulating the resistivity of the flat seam, it is possible to locate heating areas on a clothing by allowing one part of a seam to transmit the heating energy and another part to heat the wearer of the clothing, in particular by making seam interconnections using wires having different resistivity.

According to one embodiment, at least one edging wire corresponds to a metal wire. This embodiment makes it possible to further modulate the resistivity of a part of a flat seam by reinforcing the number of conductive features.

The flat seam can be sewn directly on the clothing. Alternatively, the flat seam can be made outside the clothing and affixed by adhering on the clothing after it has been completed. E.g., the flat seam can be made on a strip of fabric independent of the clothing and affixed by adhering on the clothing. It is thus possible to produce multiple flat seams having discrete properties and simply affix the desired flat seam to electrically connect a feature with a desired electrical transmission power.

According to one embodiment, said article of clothing comprises several flat seams, at least two flat seams incorporating at least one conductive wire corresponding to said connecting wire laid flat between said edging wires; said at least two flat seams being connected by a connection point between two conductive wires of said flat seams so as to create electrical continuity between said at least two flat seams.

This connection point makes it possible to use insulated wires whose insulation sheath is removed only at the connection between the two electrical wires.

In doing so, it is possible to form an electrical network on a clothing and select seams whose connections must be electrically conductive or resistive.

Additionally, it is also possible to use two wires in a seam having an interconnection point connecting the two conductive wires and forming a closed network in the seam. This network allows to use a single seam to embody a closed circuit, e.g. in order to heat a clothing.

According to one embodiment, said article of clothing comprises at least one connector electrically connected to said at least one conductive wire so as to electrically connect said flat seam with an external device. This embodiment allows the flat seam to be connected with an external device, e.g. a power supply.

According to one embodiment, said article of clothing comprises at least one sensor electrically connected to said at least one conductive wire.

This embodiment allows the flat seam to carry information from a sensor, e.g. a sensor placed in contact with the skin of the wearer of the clothing.

According to one embodiment, said article of clothing comprises at least one electrical energy consuming member electrically connected to said at least one conductive wire.

This embodiment allows the flat seam to carry electrical energy to power an energy consuming member, e.g. to turn on an LED.

According to a second aspect, the invention relates to a method for producing a flat seam between two fabrics positioned edge-to-edge; a first edge of the first fabric being sewn with a first edging wire; a second edge of the second fabric being sewn with a second edging wire; a connecting wire being sewn between the two bends so as to have a sinusoidal shape having bends alternatively connected to the first and second bend; and at least one other connecting wire extending in a discrete plane from said connecting wire laid flat.

The invention is characterized in that said connecting wire laid flat corresponds to a conductive wire suitable for transmitting an electrical current.

This second aspect of the invention relates to the method for connecting two pieces of fabric edge-to-edge without creating extra material thickness at the seam while incorporating a conductive wire.

According to one embodiment, said method comprises a step of producing an electrical connection between two conductive wires of two flat seams; the step of producing an electrical connection comprising a first step of removing a protective layer surrounding the conductive wire at the electrical connection and a second step of welding the two conductive wires. This embodiment allows the production of an electrical connection between two conductive wires so as to form a conductive network on the clothing.

BRIEF DESCRIPTION OF THE FIGURES

The way to practice the invention, and also the advantages which followed there from, will emerge clearly from the description of the following embodiments, with the support of the attached figures in which.

Of course, the dimensions and proportions of some elements constituting the invention have been deformed, exaggerated and/or separated from reality for the purpose of making the invention well understood.

METHOD FOR IMPLEMENTING THE INVENTION

Figure 1:
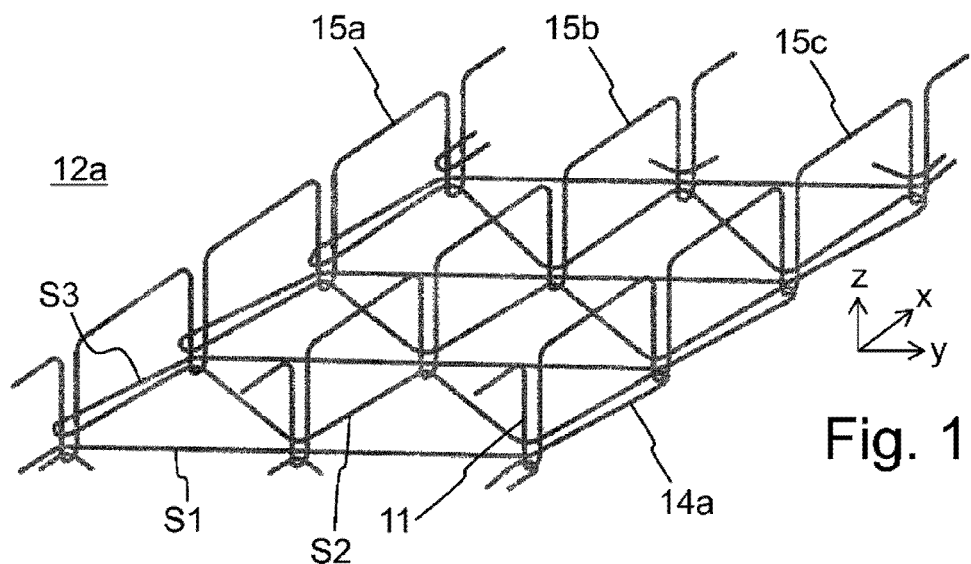
FIG. 1 is a schematic perspective depiction of a flat seam according to a first embodiment of the invention.
Figure 2:
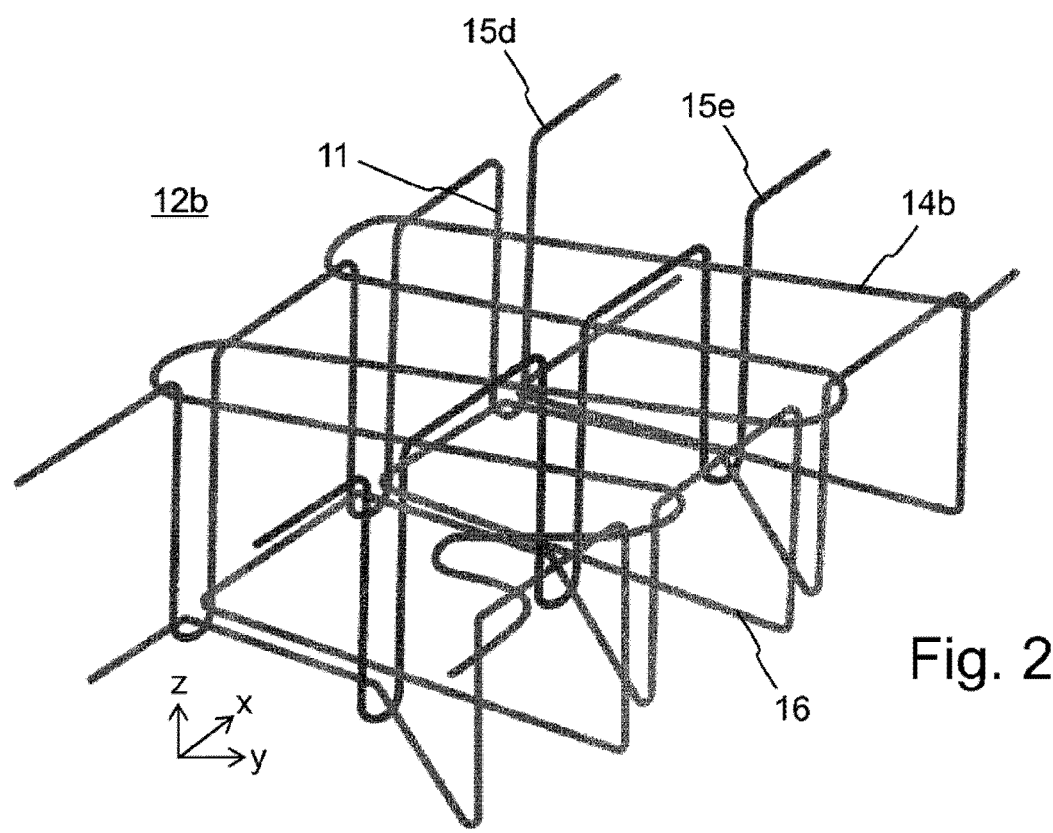
FIG. 2 is a schematic perspective depiction of a flat seam according to a second embodiment of the invention.

FIGS. 1 and 2 show two embodiments of a flat seam 12a, 12b incorporating a conductive wire 14a, 14b.

The first flat seam 12a, illustrated in FIG. 1, comprises four wires: three edging wires 15a-15c and a connecting wire 14a. Each edging wire 15a-15c extends in a weft direction x with stitches 11 forming loops in the mesh of the fabric whereupon the edging wire 15a-15c is sewn.

At each stitch 11, the edging wire 15a-15c extends in the fabric according to a direction z, orthogonal to the weft x and warp y directions of the fabric.

The three edging wires 15a-15c are stitched substantially parallel to the fabric or to several fabrics laid edge-to-edge so as to form an article of clothing. The connection between these edging wires 15a-15c is provided by a connecting wire 14a extending according to the weft x and warp y directions of the fabric at the lower ends of the stitches 11. Thus, the article of clothing has an upper side at which the three edging wires 15a-15c are visible and a lower side at which the connecting wire 14a is visible.

The connecting wire 14a has a first section S1, substantially straight, passing through each loop of stitches 11 of the three edging wires 15a-15c.

A second section S2, S-shaped, extends between two consecutive loops of stitches 11 of a first edging wire 15a-15c, and extends diagonally between two loops of two discrete edging wires 15a-15c. A last section S3 forms a mouth around the first stitch 11 until reaching a new weft of the flat seam 12a. This sewing pattern is known in Anglo-Saxon literature by the term triple wire "flat lock", referring to the three edging wires 15a-15c.

The invention is characterized in that the connecting wire 14a is sewn by a conductive wire. E.g., the conductive wire 14a may correspond to a copper wire or a copper alloy circular cross-section having a diameter of 0.2 mm. Preferably, the diameter of the conductive wire 14a is between 0.02 mm and 0.4 mm. Of course, the conductive wire 14a may be made of another conductive material without changing the invention. E.g., with a material or alloy having an electrical conductivity greater than $1 \cdot 10^6$ S·m$^{-1}$. Additionally, the conductive wire 14a may be covered with a shield and/or a sheath, e.g. grade 1 to 3 enameled protection. The conductive wire may also be made by juxtaposition of several conductive wires to the connecting wire 14a.

The flat seam may also have other topologies. E.g., the flat seam may correspond to one of the class 600 stitches of the NF ISO 4915 standard of November 2015. E.g., the invention may be implemented for points 602, 603, 604, 605, 606, 607, 608 and 609 of the NF ISO 4915 standard of November 2015.

FIG. 2 illustrates a second example of flat seam 12b corresponding to the invention. This flat seam 12b incorporates two edging wires 15d-15e and two connecting wires 14b and 16. As previously disclosed, each edging wire 15d-15e extends in a weft direction x with stitches 11 forming loops in the mesh of the fabric whereupon the edging wire 15d-15e is sewn.

At each stitch 11, the edging wire 15d-15e extends in the fabric according to direction z, orthogonal to the weft x and warp y directions of the fabric.

The connection between these edging wires 15d-15e is provided by two connecting wires 14b and 16. A connecting wire 16 extends in the three x, y and z directions of the fabric and a connecting wire 14b extends only in the frame x and warp y directions of the fabric. This sewing pattern is known in Anglo-Saxon literature by the term four-wire "flat lock", referring to the four wires forming the flat seam 12b.

The connecting wire 14b is laid flat on the fabric having loops interposed between the stitches 11 and the loops of the connecting wire 16. Thus, as disclosed with reference to FIG. 1, this connecting wire 14b can be embodied by a conductive wire.

These flat seams 12a-12b can be used for different applications without changing the invention.

E.g., they can be used to make topstitching, decorative designs on a fabric or the assembly of two fabrics, securely or not. The nature of the fabric does not matter either. E.g., flat seams 12a-12b can be adjusted to attach stretch or ultra-stretch fabrics.

This conductive wire 14a-14b, incorporated into a flat seam 12a-12b, makes it possible to transmit electrical energy into the flat seam 12a-12b. By using a single flat seam 12a-12b incorporating a conductive wire 14a-14b, it is possible to heat a part of a clothing whereupon the flat seam 14a-14b is formed.

Additionally, a flat seam 12a-12b may incorporate other wires in addition to the conductive wire 14a-14b.

In the example in FIG. 2, the connecting wire 16 may correspond to a wire having a smaller cross-section than the conductive wire 14a-14b so as to withstand the multiple bends induced by the topology of the flat seam 12b. E.g., the connecting wire 16 may correspond to a copper wire circular cross-section having a diameter of 0.3 mm. In the same way, at least one edging wire 15a-15e may correspond to a metal wire. Additionally, the wires, other than the conductive wire 14a-14b, can be incorporated on only a part of the flat seam 12a-12b so that the resistance of the flat seam 12a-12b varies depending on the number of conductive features.

Figure 3:
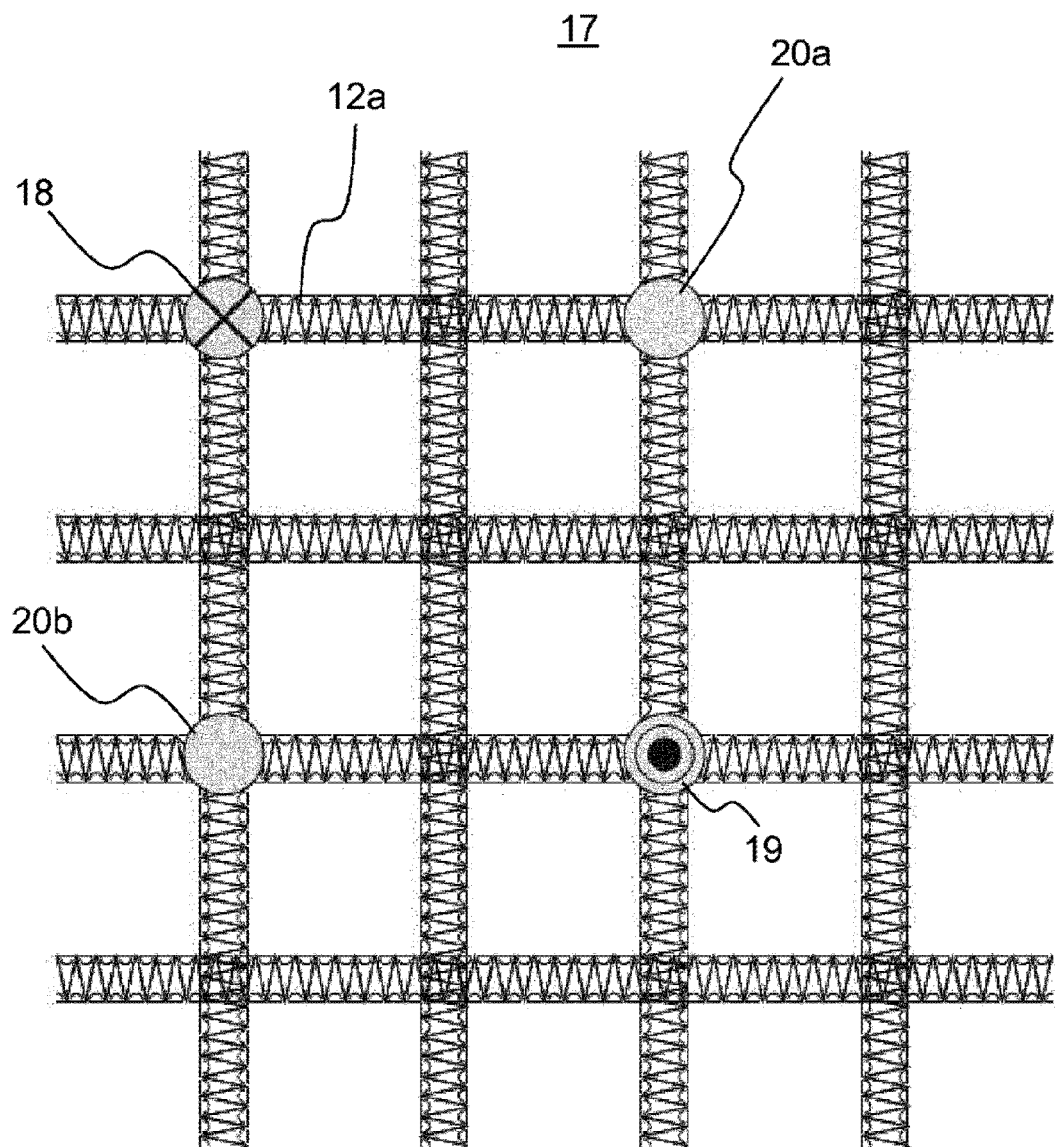
FIG. 3 is a schematic top depiction of a conductive network formed by a set of flat seams according to the embodiment of FIG. 1.

An article of clothing 10 may comprise several flat seams 12a-12b forming a conductive network 17, as illustrated in FIG. 3. In this example, the flat seams 12a-12b are arranged in the form of a network of lines and of columns. Each wire 14a-14b of each flat seam 12a-12b has a sheath so that the crossing of two flat seams 12a-12b does not directly form an electrical connection.

Several intersections of the flat seams are provided with connection points 20a-20b at which the sheath is removed and a seal is welded between the two conductive wires 14a-14b of the two flat seams 12a-12b. In addition to the connection points 20a-20b, the article of clothing 10 may comprise connectors 19 for connecting external devices to the conductive wire 14a-14b, e.g. a battery. Some interconnections may also be provided with a sensor or an electrical power consuming member 18, such as a light-emitting diode (LED).

Figure 4:
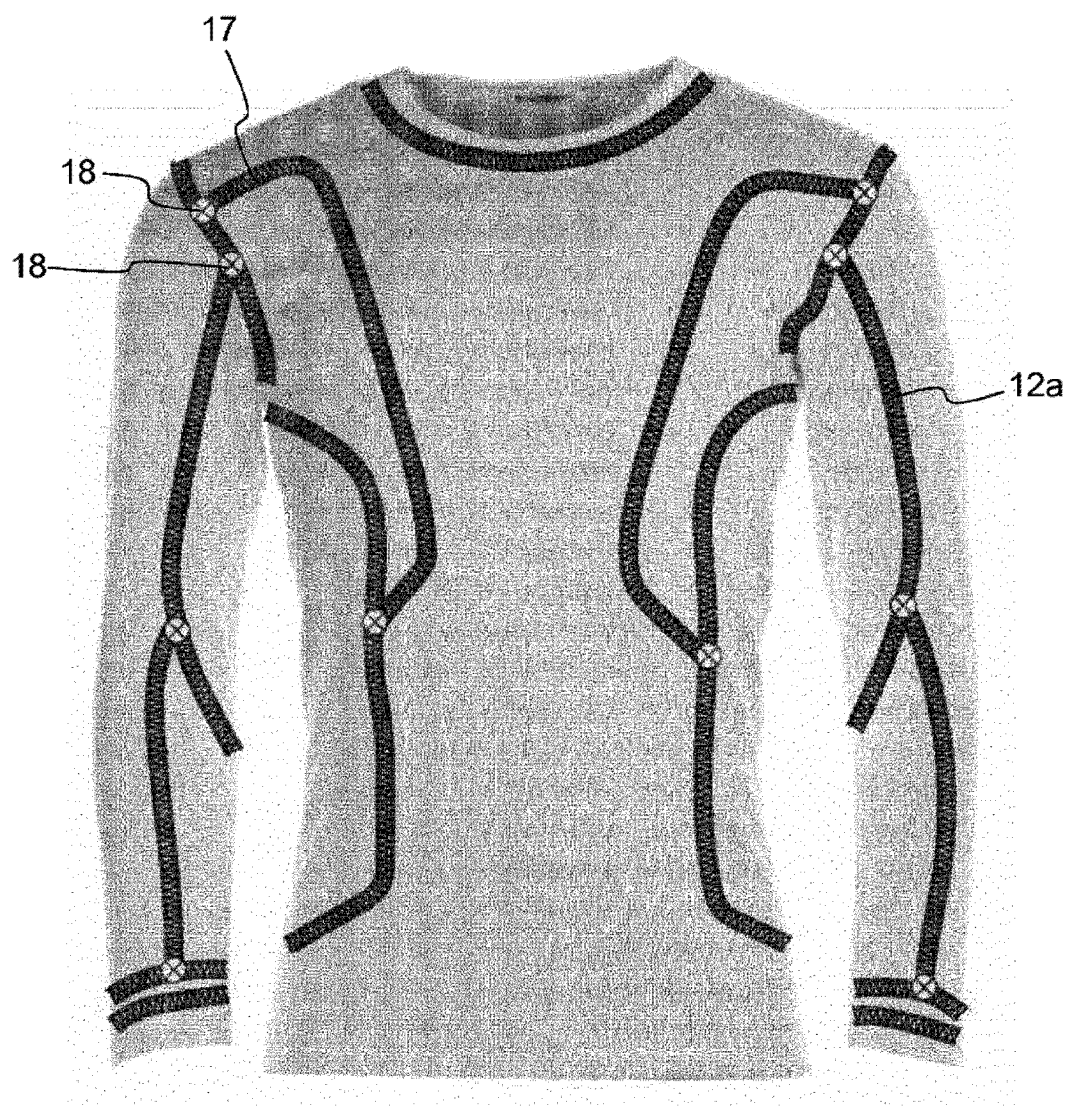
FIG. 4 is a front view of a clothing incorporating a conductive network formed by a set of flat seams according to the embodiment of FIG. 1.
Figure 5:
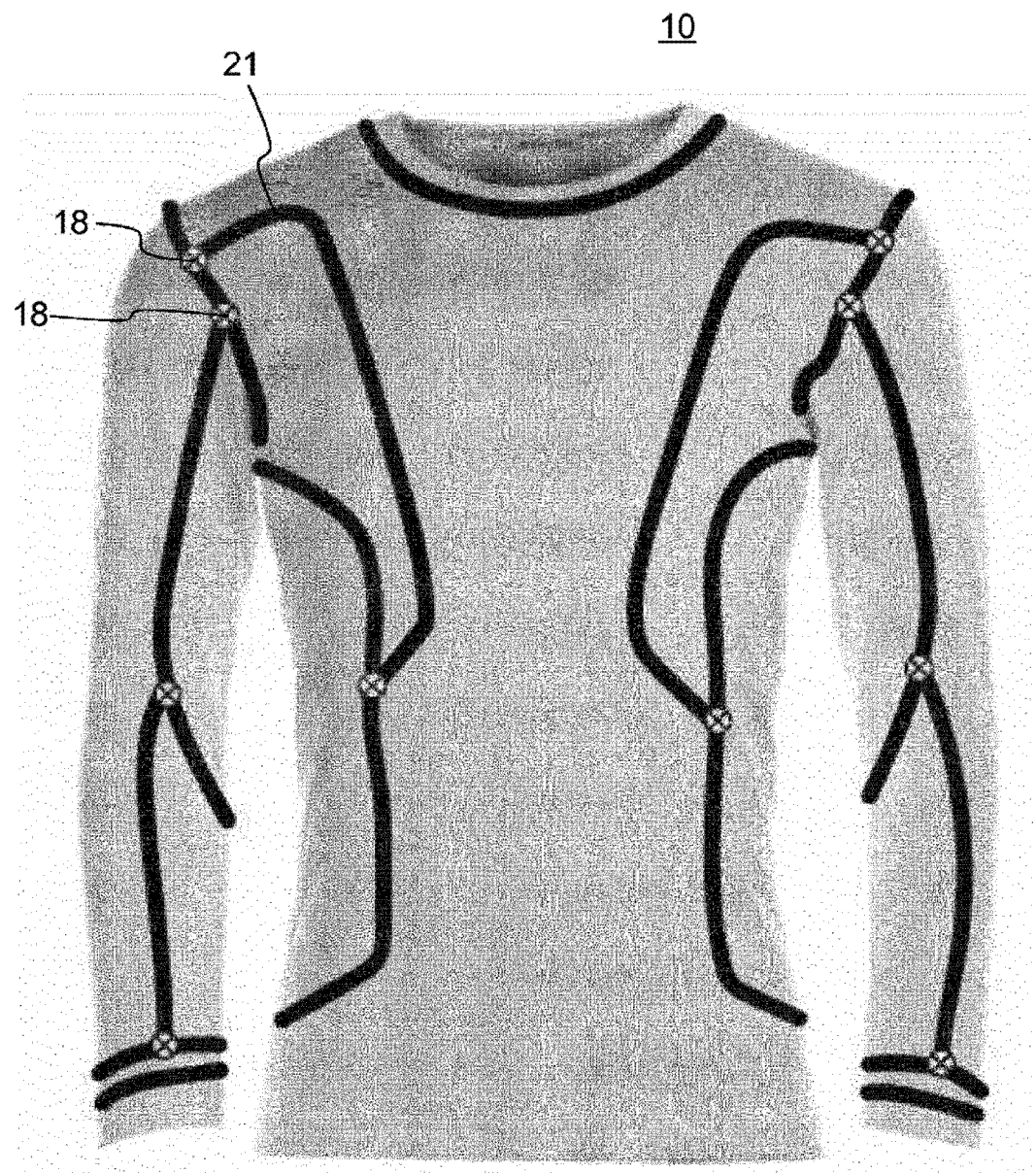
FIG. 5 is a front view of the clothing of FIG. 4 having protective strips covering the flat seams.

It is thus possible to create a clothing 10 incorporating a conductive network 17 and use this conductive network 17 according to the desired application. FIGS. 4 and 5 illustrate a clothing 10 comprising LEDs powered by a conductive network 17 arranged at the seams of the clothing 10.

Thus, the seams of the clothing 10 are made by flat seams 12a-12b incorporating at least one conductive wire 14a-14b so as to transmit electrical energy from a connector, not shown, connected to a battery up to the various LEDs. FIG. 5 illustrates a variant wherein the flat seams 12a-12b are surmounted by an insulating protective strip 21 so as to conceal and protect the flat seams.

Although the flat seams can be made directly on the clothing to incorporate the conductive wire(s), it is also possible to achieve the flat seams independently of the clothing and affix the flat seam on the clothing, e.g. by sewing the flat seam on a strip of heat-sealed fabric.

The invention thus makes it possible to produce a new type of clothing 10 comprising conductive wires 14a-14b incorporated into flat seams 12a-12b. This new type of clothing can be used to make winter sportswear, clothing incorporating light signals, or clothing for physiological analysis.

The invention claimed is:

1. An article of clothing comprising at least one conductive wire suitable for transmitting an electrical current; characterized in that said article of clothing has at least one flat seam incorporating:
    at least two substantially parallel edging wires; and
    at least one connecting wire laid flat and in a serpentine manner between said edging wires; said connecting wire having bends alternatively connected to said edging wires; said connecting wire corresponding to said at least one metal wire; and—at least one other connecting wire extending in a discrete plane from said connecting wire laid flat.

2. The article of clothing according to claim 1, wherein said at least one connecting wire disposed in a flat and serpentine manner between said edging wires is characterized by a juxtaposition of at least two metal wires.

3. The article of clothing according to claim 1, wherein said at least one other connecting wire corresponds to a metal wire.

4. The article of clothing according to claim 1, wherein said at least one edging wire corresponds to a metal wire.

5. The article of clothing according to claim 1, wherein said at least one flat seam is affixed by adhering on said article of clothing.

6. The article of clothing according to claim 5, wherein said at least one flat seam is sewn on a strip of fabric, said strip of fabric being affixed by adhering on said article of clothing.

7. The article of clothing according to claim 1, wherein said article of clothing comprises several flat seams, at least two flat seams incorporating at least one conductive wire corresponding to said connecting wire laid flat between said edging wires; said at least two flat seams being connected by a connection point between two conductive wires of said flat seams so as to create electrical continuity between said at least two flat seams.

8. The article of clothing according to claim 1, wherein said article of clothing comprises at least one connector electrically connected to said at least one conductive wire so as to electrically connect said flat seam with an external device.

9. The article of clothing according to claim 1, wherein said article of clothing comprises at least one sensor electrically connected to said at least one conductive wire.

10. The article of clothing according to claim 1, wherein said article of clothing comprises at least one electrical energy consuming member electrically connected to said at least one conductive wire.

11. A production method for producing a flat seam between two fabrics positioned edge-to-edge; a first edge of the first fabric being sewn with a first edging wire; a second edge of the second fabric being sewn with a second edging wire; and a connecting wire being sewn between the two edging wires so as to have a sinusoidal shape having bends alternatively connected to the first and second edging wires; said flat seam also comprising at least one other connecting wire extending in a discrete plane from said connecting wire laid flat, characterized in that said connecting wire corresponds to a conductive wire suitable for transmitting an electrical current.

12. The production method according to claim 11, wherein said method comprises a step of producing an electrical connection between two conductive wires of two flat seams; the step of producing an electrical connection having a first step of removing a protective layer surrounding the conductive wires at the electrical connection and a second step of welding the two conductive wires.

* * * * *